United States Patent [19]

Brunner et al.

[11] Patent Number: 5,568,722
[45] Date of Patent: Oct. 29, 1996

[54] EMISSION PROBE FOR THE REMOVAL OF EXHAUST GAS FROM THE COMBUSTION CHAMBER OF A GAS TURBINE

[75] Inventors: Philipp Brunner, Hunzenschwil; Rudolf Tresch, Seon, both of Switzerland

[73] Assignee: ABB Management AG, Baden, Switzerland

[21] Appl. No.: 414,743

[22] Filed: Mar. 31, 1995

[30] Foreign Application Priority Data

Jun. 22, 1994 [DE] Germany ............... 44 21 807.9

[51] Int. Cl.$^6$ ........................................ F02C 7/00
[52] U.S. Cl. ................ 60/39.33; 73/863.11; 415/118
[58] Field of Search ........................ 60/39.02, 39.33;
 73/23.4, 23.41, 23.42, 863.11, 864.73, 864.74;
 415/118

[56] References Cited

U.S. PATENT DOCUMENTS

| | | | |
|---|---|---|---|
| 3,085,435 | 4/1963 | Miscoe et al. | 73/863.11 |
| 4,244,222 | 1/1981 | Hoyer et al. | 415/118 |
| 4,283,947 | 8/1981 | George et al. | 73/863.11 |
| 4,756,200 | 7/1988 | Ramsner et al. | 73/863.11 |
| 5,404,760 | 4/1995 | Robinson et al. | 73/863.11 |

FOREIGN PATENT DOCUMENTS

| | | |
|---|---|---|
| 2048184 | 4/1971 | Germany . |
| 2343470 | 3/1974 | Germany . |
| 1557970 | 12/1979 | United Kingdom . |

*Primary Examiner*—Louis J. Casaregola
*Attorney, Agent, or Firm*—Burns, Doane, Swecker & Mathis

[57] ABSTRACT

In an emission probe (11, 21) for the removal of exhaust gas from the combustion chamber of a gas turbine, comprising a one-piece probe tube (12, 22, 31, 41) which, in its interior, has an emission passage (13, 24, 32, 42) extending in the direction of the tube axis and two cooling passages (14a,b; 25; 25a,b; 34a,b; 45a,b) extending parallel to the emission passage (13, 24, 32, 42) and adjacent to one another, optimum cooling in combination with simple construction is achieved by virtue of the fact that, as seen in cross section, the cooling passages (25; 25a,b; 34a,b; 45a,b) at least partially enclose the emission passage (24, 32, 42) and occupy the interior of the probe tube (22, 31, 41) to an extent such that the wall thickness of the tube wall (212; 38; 48) between the cooling passages (25; 25a,b; 34a,b; 45a,b) and the external space surrounding the probe tube (22, 31, 41) is approximately constant over the majority of the tube circumference, and wherein a plurality of cooling ribs (210; 35; 44) is provided, which project from the tube wall (212; 38; 48) into the interior of the cooling passages (25; 25a,b; 34a,b; 45a,b).

7 Claims, 2 Drawing Sheets

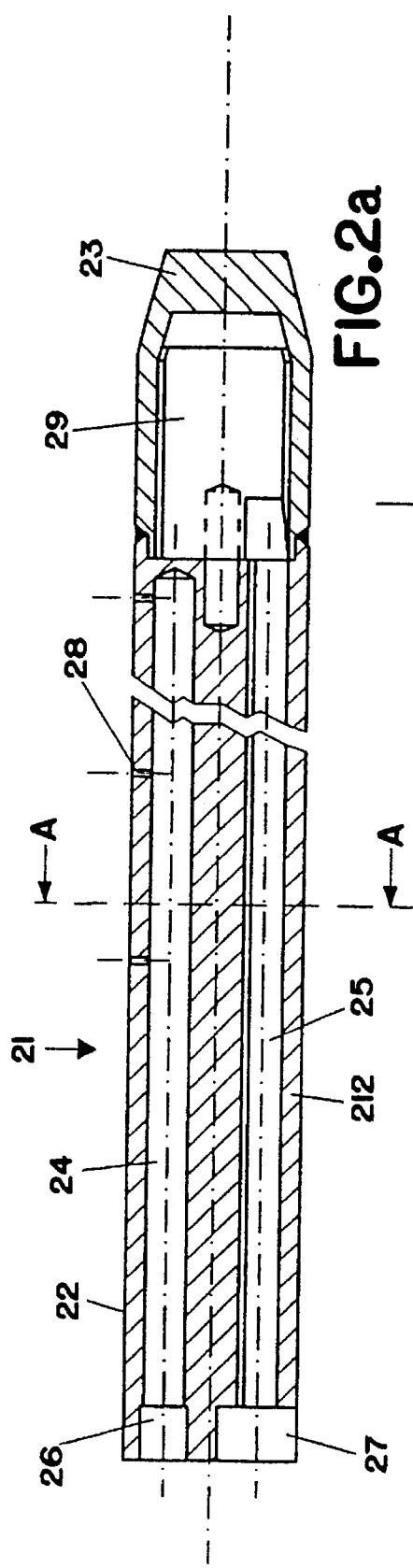
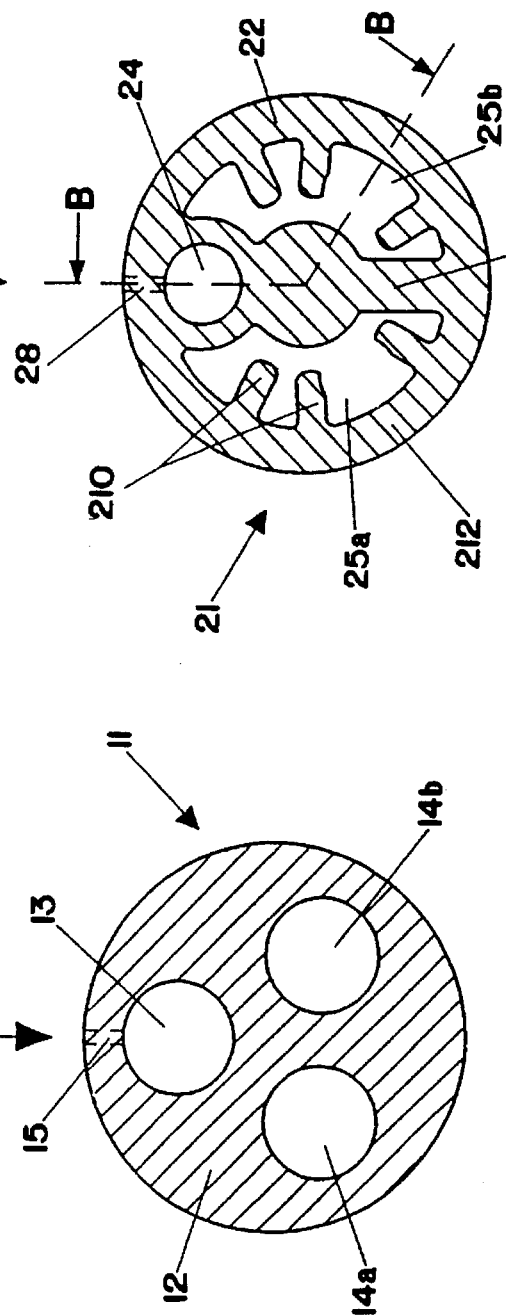
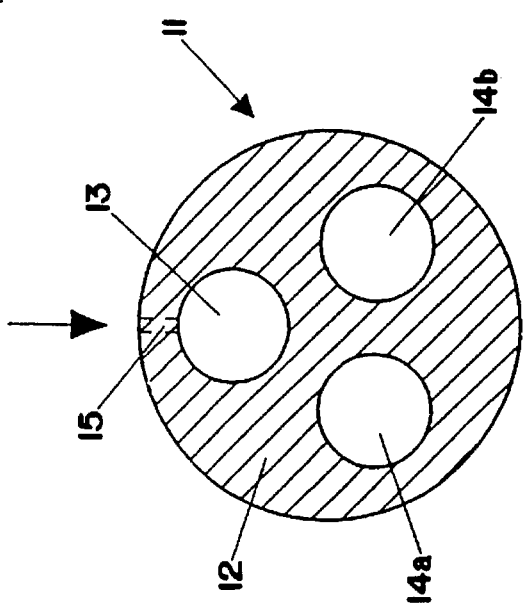

EMISSION PROBE FOR THE REMOVAL OF EXHAUST GAS FROM THE COMBUSTION CHAMBER OF A GAS TURBINE

BACKGROUND OF THE INVENTION

1. Field of the Invention

The present invention relates to the field of gas turbines. It relates to an emission probe for the removal of exhaust gas from the combustion chamber of a gas turbine, comprising a one-piece probe tube which, in its interior, has an emission passage extending in the direction of the tube axis and two cooling passages extending parallel to the emission passage and adjacent to one another.

An emission probe of this kind has already been used in practice.

2. Discussion of Background

Emission or exhaust-gas probes are used in the case of combustion processes wherever it is necessary to determine and monitor the effectiveness of the combustion process itself and the pollutant content of the exhaust gases. Problems arise here, in particular, from the generally high exhaust-gas temperatures, which in the case of gas turbines, for example, can be well above 1000° C. and, on the one hand, stress the probe itself and, on the other hand, can alter in an undesirable manner the exhaust-gas samples removed (e.g. due to secondary chemical reactions).

Patent Specification GB-B-1 557 970 has already disclosed an exhaust-gas probe for a gas turbine which is constructed from a plurality of tubes situated one inside the other, the inner gas removal tube being surrounded by a plurality of concentrically arranged cooling passages. The known exhaust-gas probe is of very complex construction because different individual tubes have to be assembled in a manner which will withstand the high operating temperatures, At the same time, this manner of construction makes integration into existing components of the gas turbine more difficult.

An emission probe of simpler construction, as depicted in cross section in FIG. 1, has furthermore been used in practice. The emission probe 11 comprises a one-piece probe tube 12 in which an emission passage 13 and two cooling passages 14a, b of approximately the same cross section are arranged parallel to the tube axis at the corners of an isosceles triangle. For the purpose of removing samples, the emission passage 13 is connected by removal holes 15 to the external space of the probe. The probe is installed with its axis transverse to the flow of exhaust gas, with the result that the exhaust gas flows around the probe. The probe is oriented in such a way that the outer openings of the removal holes 15 lie directly at the stagnation point of the flow. The direction of flow is indicated in FIG. 1 (as also in FIG. 2b) by a vertical arrow.

Probes of this kind have already been used under high pressure in combustion-chamber tests, but the cooling was insufficient for the requirements because the cooling passages comprised cylindrical longitudinal holes. As a result, the cooling effect was limited and the zones which were furthest away from the cooling passages were rapidly overheated. This applies particularly to the portion at the stagnation point where the holes for exhaust-gas removal are situated. A further disadvantage of the old design is the fact that the probes are permanently warped by differential thermal expansions.

SUMMARY OF THE INVENTION

Accordingly, one object of the invention is to provide a novel emission probe for gas turbines which, while being of simple construction, has optimum cooling and hence has a long life, does not suffer any thermally induced warping and prevents alteration of the exhaust-gas samples removed, and to indicate a method for the production of said probe.

This object is achieved in the case of an emission probe of the type stated at the outset by virtue of the fact that, as seen in cross section, the cooling passages at least partially enclose the emission passage and occupy the interior of the probe tube to an extent such that the wall thickness of the tube wall between the cooling passages and the external space surrounding the probe tube is approximately constant over the majority of the tube circumference, and wherein a plurality of cooling ribs is provided, which project from the tube wall into the interior of the cooling passages.

The heart of the invention is the optimization of the heat transfer in the one-piece probe tube both between the cooling passages and the emission passage and between the cooling passages and the outer wall of the tube by means of a suitable cross sectional geometry of the passages and the use of cooling ribs.

According to a first preferred embodiment of the invention, the cooling ribs are each arranged perpendicular to the tube wall and are formed integrally on the tube wall, the cooling ribs have an essentially rectangular cross section, and, in their longitudinal direction, the cooling ribs extend parallel to the probe axis. While providing good cooling, this ensures that the probe is simpler to manufacture.

A second preferred embodiment of the invention is distinguished by the fact that the emission passage is arranged at the boundary of the probe tube and is connected to the external space by a plurality of removal holes, and that the cooling passages are arranged underneath the emission passage on both sides of, and in mirror symmetry with respect to, a center plane extending through the emission passage. The symmetrical arrangement of the cooling passages, in particular, leads to further equalization of the temperature distribution in the probe.

A third preferred embodiment of the probe according to the invention is distinguished by the fact that the emission passage ends within the probe tube in the manner of a blind hole, that the cooling passages pass through the probe tube and open into the closed deflection space of a probe cap which closes off the probe tube at its end situated in the combustion chamber, and that connections for the emission passage and the cooling passages are provided at the other end of the probe tube. By means of this construction, it is possible to further simplify manufacture.

Further embodiments emerge from the dependent claims.

The method according to the invention for the production of the probe is distinguished by the fact that the cooling passages together with their cooling ribs are machined from a solid tube by spark erosion, preferably by wire spark erosion.

According to the invention, the probe is used in the case of a gas turbine with sequential combustion to measure and monitor the exhaust emissions after the first combustion chamber, the measurement results obtained preferably being used to control the gas turbine for the purpose of optimizing the combustion process and to obtain low pollutant emissions.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows a cross section through an emission probe which has already proven itself in practice;

FIG. 2a illustrates in longitudinal section a first exemplary embodiment of an emission probe according to the invention;

FIG. 2b illustrates in cross section the probe of FIG. 2a.

DESCRIPTION OF THE PREFERRED EMBODIMENTS

Figure 3:
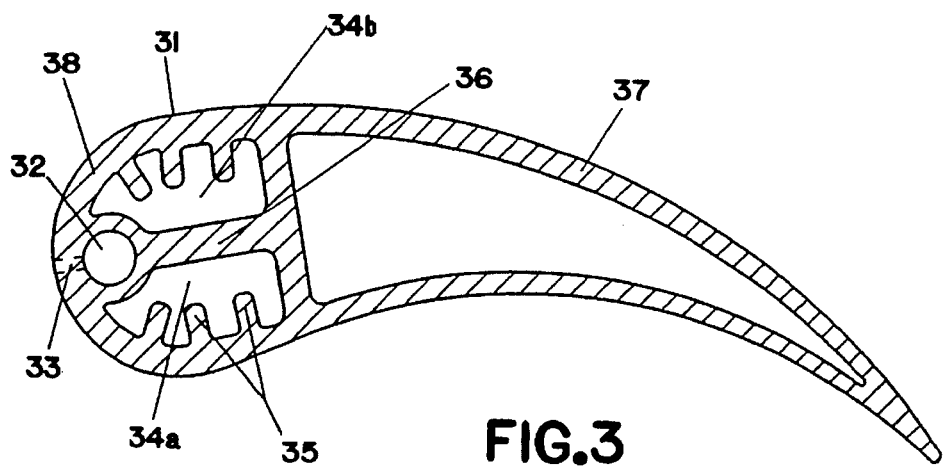
FIG. 3 shows an exemplary embodiment of a probe according to the invention integrated into a turbine guide vane.

Referring now to the drawings, wherein like reference numerals designate identical or corresponding parts throughout the several views, a preferred exemplary embodiment of an emission probe according to the is shown in longitudinal section in FIG. 2a taken along the line B—B of FIG. 2b and in cross section in FIG. 2b taken along the line A—A of FIG. 2a. The emission probe 21 essentially comprises a probe tube 22 and a probe cap 23 which is welded to that end of the probe tube 22 which projects into the combustion chamber. Arranged within the probe tube 22 there are, in the upper half, an emission passage 24 (of circular aperture cross section) and, underneath it, two cooling passages 25 or, more specifically, 25a and 25b.

Figure 4:
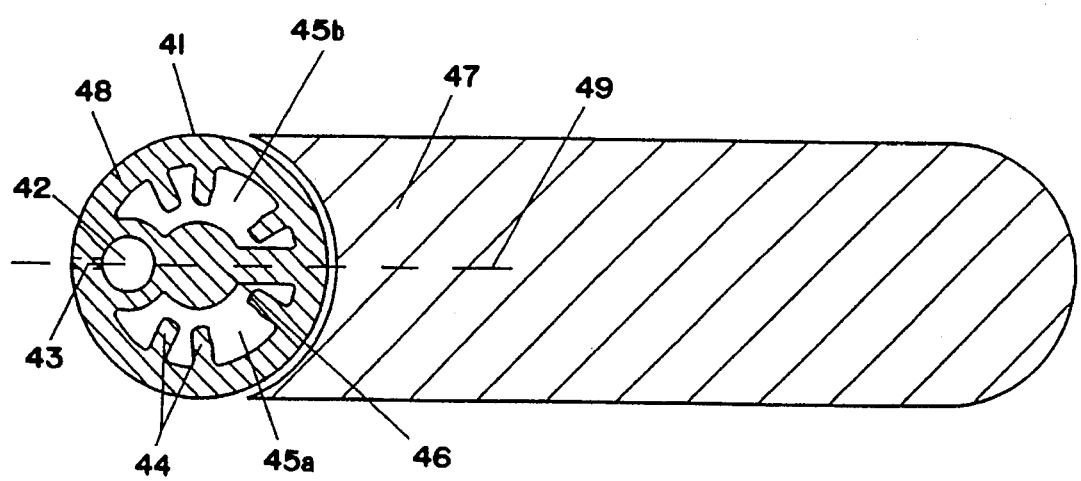
FIG. 4 shows an exemplary embodiment of a probe according to the invention integrated into a rib within the turbine.

As seen in cross section (FIG. 2b), the cooling passages 25a, b partially enclose the emission passage 24 and are separated from it by a relatively thin, uniform wall, with the result that the heat transfer between the emission passage 24 and the cooling passages 25a, b is considerably improved compared with the arrangement in FIG. 1. A comparable reduction and equalization of the wall thickness is also carried out between the cooling passages 25a, b and the external space around the probe. To achieve this—as can be seen in FIG. 2b—the cooling passages 25a, b occupy the interior of the probe tube 22 to an extent such that the wall thickness of the tube wall 212 is approximately constant over the majority of the tube circumference. In this arrangement, they are arranged in mirror symmetry with respect to a center plane (49 in FIG. 4) extending through the emission passage 24. Overall, the probe tube is hollowed out to a greater extent than in FIG. 1, thereby simultaneously providing a larger cross section of flow for the cooling medium. A dividing wall 211 is, of course, left between the cooling passages 25a, b.

Particularly important for the improved heat transfer between the tube wall 212 and the cooling passages 25a, b are additional cooling ribs 210. The cooling ribs 210 are each arranged perpendicular to the tube wall 212 and are formed integrally on the tube wall. They have an essentially rectangular cross section and, in their longitudinal direction, extend parallel to the probe axis. By virtue of this ribbing, the cooling is sufficient to allow the probe to be used reliably even under extreme thermal loads.

The comparatively thin-walled embodiment of the probe and the ribbing of the cooling passages result in optimum cooling, which leads to the following advantages:

A long service life of the probe is obtained by virtue of the low operating temperature Oxidation and melting of the probe at the stagnation point are prevented;

Warping of the probe by differential thermal expansion is prevented;

The exhaust gas removed is cooled to an extent such that secondary chemical reactions (burn-up of CO, UHC, conversion of NO to $NO_2$ and all other possible reactions not mentioned here) are prevented; this makes it possible to analyze the actual exhaust-gas composition at the location of sampling, i.e. at the location of the probe.

For the purpose of removing the exhaust-gas samples, the emission passage 24 is connected to the external space by means of a multiplicity of removal holes 28, which end at the stagnation point of the probe, around which flow is occurring. The emission passage 24 ends within the probe tube 22 in the manner of a blind hole (FIG. 2a). The cooling passages 25a, b, on the other hand, pass through the probe tube 22 and open into a closed deflection space 29 of the probe cap 23. Here, the cooling medium (water or the like) flowing in one direction through one cooling passage is deflected and flows back in the opposite direction in the other cooling passage. Provided at the other end of the probe tube are connections 26, 27 for the emission passage 24 and the cooling passages 25a, b.

Since the cooling passages 25a, b with their complex boundary geometry (cooling ribs) extend with unvarying cross section through the entire probe tube 22, they can be machined in a particularly advantageous manner from a solid tube by spark erosion, especially by wire spark erosion. Almost any ribbing and passage contours can be achieved by this method of manufacture.

In principle, the emission probe according to the invention can be used as a completely independent probe in a gas turbine. However, it is also conceivable to design the probe tube as an integral part of a combustion-chamber or gas-turbine component exposed to hot gas. Two exemplary embodiments of such integration are shown in cross section in FIGS. 3 and 4. In the exemplary embodiment of FIG. 3, the probe tube 31 with the emission passage 32, the removal holes 33, the cooling passages 34a, b, the cooling ribs 35, the dividing wall 36 and the tube wall 38 is integrated into the front part of a turbine guide vane. It is self-evident that the circular cross sectional geometry has here been sacrificed in favor of the specific vane geometry. In the exemplary embodiment of FIG. 4, the probe tube 41 with the emission passage 42, the removal holes 43, the cooling ribs 44, the cooling passages 45a, b, the dividing wall 46 and the tube wall 48 is integrated into a rib 47 (exposed to hot gas). The probe tube can, of course, also be part of other components.

The emission probe described above can, in general terms, be employed with various gas turbines or even other combustion processes. However, it is employed specifically in the case of a gas turbine with sequential combustion to measure and monitor the exhaust emissions after the first combustion chamber. The measurement results obtained in this process are then preferably used to control the gas turbine for the purpose of optimizing the combustion process and to obtain low pollutant emissions.

Overall, the invention provides a simple, operationally reliable and optimally cooled emission probe of compact construction.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An emission probe for the removal of exhaust gas from the combustion chamber of a gas turbine, comprising a one-piece probe tube having an outer tube wall and a longitudinal axis, and being formed with an interior emission passage extending along the longitudinal axis and two interior cooling passages extending parallel to the emission passage and adjacent to one another, wherein, in transverse cross section, the cooling passages at least partially surround the emission passage, and wherein a thickness of the tube wall enclosing the cooling passages is approximately constant over a majority of the tube circumference, and wherein a plurality of cooling ribs project from the tube wall into the cooling passages.

2. The emission probe as claimed in claim 1, wherein each of the cooling ribs is disposed perpendicular to the tube wall and is formed integrally on the tube wall, wherein the cooling ribs have a substantially rectangular cross section, and wherein, the cooling ribs extend parallel to the longitudinal axis.

3. The emission probe as claimed in claim 1, wherein the emission passage is partially defined by the outer tube wall and a plurality of removal holes are provided through the outer tube wall connecting to the emission passage, and wherein the cooling passages are arranged adjacent to the emission passage and symmetrical to a longitudinal center plane extending through the emission passage.

4. The emission probe as claimed in claim 1, wherein the emission passage ends within the probe tube as a blind hole, wherein the emission probe further comprises a probe cap having a deflection space attached to a first end of the tube, the cooling passages extending to the closed deflection space, and wherein connections for communicating with the emission passage are provided at an opposite end of the probe tube.

5. The emission probe as claimed in claim 1, wherein the probe tube comprises an integral part of one of a combustion chamber component and gas-turbine component exposed to hot gas.

6. The emission probe as claimed in claim 5, wherein the component exposed to hot gas is a turbine guide vane.

7. The emission probe as claimed in claim 5, wherein the component exposed to hot gas is a rib.

* * * * *